United States Patent [19]
Trent et al.

[11] Patent Number: 5,428,131
[45] Date of Patent: Jun. 27, 1995

[54] ARCHAEBACTERIAL CHAPERONIN-MEDIATED PROTEIN STABILIZATION

[75] Inventors: Jonathan D. Trent, Guilford; Arthur L. Horwich, Westport, both of Conn.

[73] Assignee: Yale University, New Haven, Conn.

[21] Appl. No.: 116,098

[22] Filed: Sep. 2, 1993

Related U.S. Application Data

[63] Continuation of Ser. No. 756,627, Sep. 9, 1991, abandoned, which is a continuation-in-part of Ser. No. 721,974, Jun. 27, 1991, which is a continuation-in-part of Ser. No. 673,158, Mar. 18, 1991, which is a continuation of Ser. No. 261,573, Oct. 24, 1988, abandoned.

[51] Int. Cl.⁶ ............................................. C07K 1/06
[52] U.S. Cl. ................................... 530/350; 530/412; 530/427; 530/820; 530/402; 435/69.1; 536/23.7
[58] Field of Search ................. 530/350, 412, 820; 435/69.1; 536/23.7

[56] References Cited

U.S. PATENT DOCUMENTS 4,468,464  8/1984  Cohen et al. ..................... 435/320.1

OTHER PUBLICATIONS

R. C. Nicholson et al. Biosci Rep 4:963 1984.
Raymond J. Deshaies, Bruce D. Koch et al. "A subfamily of stress proteins facilitates translocation of secretory and mitochondrial precursor polypeptides" Nature: vol. 332 28 Apr. 1988 pp. 800–805.
Pil-Jung Kang, Joachim Osterman, et al. "Requirement for hsp70 in the mitochondrial matrix for translocation and folding of precursor proteins" Nature: vol. 348 8 Nov. 1990 pp. 137–143.
Sean M. Hemmingsen, Carol Woolford, et al :"Homologous plant and bacterial proteins chaperone oligomeric protein assembly" Nature: vol. 333 26 May 1988 pp. 330–334.
Eileen Hickey, Susan E. Brandon, et al., "Molecular cloning of sequences encoding the human heat-shock proteins and their expression during hyperthermia" Elsevier Science Publishers Gene 43 1986 pp. 147–154.
L. A. Moran, M. Chauvin, et al., "The major heat-shock protein (hsp70) gene family: related sequences in mouse, Drosophila, and yeast" Cell. Biol. 61 Nov. 18, 1982 pp. 488–499.
Thomas D. Ingolia, et al. "Saccharomyces cerevisiae Contains a Complex Multigene Family Related to the Major Heat Shock-Inducible Gene of Drosophila" Molecular and Cell. Biology, Nov. 1982 vol. 2, #11 pp. 1388–1398.
Costa P. Georgopoulos and Barbar Hohn "Identification of a host protein necessary for bacteriophage morphogenesis (the groE gene product)" Proc. Natl. Acad. Sci USA vol. 75, No. 1, pp. 131–135 Jan. 1978.
Thomas H. Lubben, et al. "Identification of a groES-like in mito-chondria that facilitates protein folding" Proc. Natl. Acad. Sci Vil. 87, pp. 7683–7687, Oct. 1990.
Gabriele T. Mues, et al., "A Human Gene Family with Sequence Homology to Drosophila melanogaster Hsp70 Heat Stoch Genes" The Journal of Biological Chemistry, vol. 261, No. 2 Jan. 15 1986 pp. 874–877.
John Ellis "Cytosolic chaperonin confirmed" Nature: vol. 358. 16 Jul. 1992 pp. 191–193.
Hugh R. B. Pelham "Speculations on the Functions of the Major Heat Shock and Gloucose-Regulated Proteins" Nature: Cell, vol. 46 Sep. 26, 1986 pp. 959–961.

(List continued on next page.)

Primary Examiner—Garnette D. Draper
Assistant Examiner—Lorraine Spector
Attorney, Agent, or Firm—Arnall Golden & Gregory

[57] ABSTRACT

TF55 is a homooligomeric complex of two stacked rings, closely resembling the quaternary structure of the chaperonins, groEL, hsp60, and RUBISCO-binding protein. Most rings of TF55 contain 9 radially arranged members. The TF55 complex binds unfolded polypeptides in vitro, preventing aggregation at elevated temperature, and exhibits ATPase activity, features consistent with its function as a molecular chaperone. At the level of primary structure, TF55 is not significantly related to the chaperonins but is highly homologous (36–40% identity) to a ubiquitous eukaryotic protein, t complex polypeptide 1 (PCT1).

7 Claims, 6 Drawing Sheets

OTHER PUBLICATIONS

Jorg Martin, Thomas Langer, Raina Boteva, Andrea Schramel, Arthur L. Horwich & F. Ilrich Hartl "Chaperonin-mediated protein folding at the surface of groeEL through a 'molten globule'-like intermediate" Nature: vol. 352 Jul 1991 pp. 36–42.

J. R. Sampson, F. X. Sullivan, L. S. Behlen, A. B. DiRenzo, and O. C. Uhlenbeck "Characterization of Two RNA catalyzed RNA Cleavage Reactions" Nature: vol. LII Feb. 1987 pp. 267–275.

Arthur L. Horwich, Walter Neupert and Franz-Ulrich Hartl "Protein-catalysed protein folding" Nature: vol. 8 No. 5 pp. 126–131 (May 1990).

Jonathan D. Trent, Elmar Nimmesgern, Joseph S. Wall, F. Ulrich Hartl & Arthur L. Horwich "A molecular chaperone from a thermophilic archaebacterium is related to the eukaryotic protein t-complex polypeptide-1" Nature: vol. 354 12 Dec. 1991 pp. 490–493.

Geoffrey North "A cytoplasmic Chaperonin?" Nature: vol. 354 12 Dec. 1991 pp. 434–435.

Ming Y. Cheng, et al "The mitochondrial chapeenonin hap60 is required for its own assembly" Nature, vol. 348 No. 6300 pp. 455–458 29th Nov. 1990.

Cheng et al. "Mitochondrial heat-shock protein hsp60 is esential for assembly of proteins imported into yeasl mitochondin" *Nature* 337, 620–625 (1989).

Fischer, G., et al., "The Mechanism of Protein Folding, Implications of in Vitro Refolding Models for de Novo Protein Folding and Translocation in the Cell" *Biochemistry* 29:2206–2212 (1990).

Freedman, Robert B., "Protein Disulfide Isomerase: Multiple Roles in the Modification of Nascent Secretory Proteins" *Cell* 57:1069–1072 (1989).

Ellis, R. John, et al., "Molecular Chaperones" *Annu. Rev. Biochem.* 60:321–347 (1991).

Dingwall, C. K., et al., "Nucleoplasmin: the archetypal molecular chaperone" *Seminars in Cell Biol.* 1:11–17 (1990).

Rothman, James E., "Polypeptide Chain Binding Proteins: Catalysts of Protein Folding and Related Processes in Cells" *Cell* 59:591–601 (1989).

Langer, T., et al., "Heat Shock Proteins hsp60 and hsp70: Their Roles in Folding, Assembly and Membrane Translocation of Proteins" *Curr. Topics in Microbiol. and Immun.* 167:3–30 (1991).

Pelham, Hugh, "Heat-shock proteins: Coming in from the cold" *Nature* 332:776–777 (1988).

Hartl, F.-U., "Heat shock proteins in protein folding and membrane translocation" *Seminars in Immunol.* 3:5–16 (1991).

Sternberg, N., "Properties of a Mutant of *Escherichia coli* Defective in Bacteriophage ∂ Head Formation (groE)" *J. Molec. Biol.* 76:25–44 (1973).

Bochkareva, E. S., et al., "Transient association of newly synthesized unfolded proteins with the heat-shock GroEL protein" *Nature* 336:254–257 (1988).

Van Dyk, Tina K., et al., "Demonstration by genetic suppression of interaction of GroE products with many proteins" *Nature* 342:451–453 (1989).

Lecker, Stewart, et al., "Three pure chaperone proteins of *Escherichia coli*-SecB. trigger factor and GroEL-form soluble complexes with precursor proteins in vitro" *EMBO, J.* 8:2703–2709 (1989).

Laminet, Axel A., et al., "The *Escherichia coli* heat shock proteins GroEL and GroES modulate the folding of the β-lactamase precursor" *EMBO, J.* 9:2315–2319 (1990).

Bucher, et al., "GroE Facilitates Refolding of Citrate Synthase by Suppressing Aggregation" *Biochemistry* 30:1586–1591 (1991).

Barraclough, Roger, et al., "Protein Synthesis in Chloroplasts: IX, Assembly of Newly-Synthesized Large Subunits into Ribulose Bisphosphate Carboxylase in Isolated Intact Pea Chloroplasts" *Biochim. Biophys. Acta* 608:19–31 (1980).

Musgrove, Janet E., et al., "Dissociation of the ribulose-bisphosphate-carboxylase large-subunit binding protein into dissimilar subunits" *Eur. J. Biochem.* 163:529–534 (1987).

Gatenby, Anthony A., et al., "Chaperone Function: The Assembly of Ribulose Bisphosphate Carboxylase-Oxygenase" *Rev. Cell Biol.* 6:125–149 (1990).

Ostermann, Joachim, et al., "Protein folding in mitochondria requires complex formation with hsp60 and ATP hydrolysis" *Nature* 341:125–130 (1989).

Chandrasekhar, Gujuluva N., et al., "Purification and Properties of the groES Morphogenetic Protein of *Escherichia coli* " *J. Biol. Chem.* 261:12414–12419.

Viitanen, Paul V., et al., "Chaperonin-Facilitated Refolding of Ribulosebisphosphate Carboxylase and ATP Hydrolysis by Chaperonin 60 (groEL) are $K^+$ Dependent" *Biochemistry* 29:5665–5670 (1990).

P. Goloubinoff et al. Nature 342:884 Dec. 21/28 1989.

ARCHAEBACTERIAL CHAPERONIN-MEDIATED PROTEIN STABILIZATION

BACKGROUND OF THE INVENTION

This is a continuation of U.S. Ser. No. 07/756,627, now abandoned, entitled "Archaebacterial Chaperonin-Mediated Protein Stabilization" filed Sep. 9, 1991, by Jonathan D. Trent and Arthur L. Horwich, which is a continuation-in-part of U.S. Ser. No. 07/721 974, abandoned in favor of U.S. Ser. No. 08/247,652,entitled "Chaperonin-Mediated Protein Folding" filed Jun. 27, 1991 by Franz-Ulrich Hartl and Arthur L. Horwich, which is a continuation-in-part of U.S. Ser. No. 07/673,158 entitled "Yeast Heat Shock Protein 60 and Analogs" filed Mar. 18, 1991 by Arthur L. Horwich, Mingyuan Cheng, Richard Hallberg, Donald S. Reading, and Alan Myers, which is a continuation of U.S. Ser. No. 07/261,573 filed Oct. 24, 1988, now abandoned.

Little is known about the mechanisms by which newly-synthesized proteins fold inside cells. Recent findings suggest that, for many proteins, folding in vivo may not be a spontaneous process. For example, while in vitro folding reactions are carried out on completed polypeptide chains, these studies fail to address the situation faced with proteins synthesized in intact cells. In the cell, the $NH_2$-terminal epitopes of a nascent protein, which are required for the protein folding, may already have emerged from a ribosome, before the remaining COOH-terminal portion of the protein has been synthesized. Similarly, the $NH_2$-terminal portion of a translocated polypeptide may emerge from the trans-side of a membrane before the COOH-terminal portion has translocated. In such instances, a "chaperoning" function is required to prevent illegitimate intra- and intermolecular interactions of the nascent polypeptides.

A number of components have been identified which are involved in mediating protein folding in a variety of cell types and compartments, as reported by Fischer, G. & Schmid, F. X. *Biochemistry* 29, 2206-2212 (1990); Freedman, R. B. *Cell* 57, 1069-1072 (1989); and Ellis and van der Vinn, *Annu. Rev. Biochem.* 60:337-347 (1991). They have been classified as "molecular chaperones" by Dingwall, C. K. & Laskey, R. A. *Seminars in Cell Biol.* 1, 11-17 (1990), or "polypeptide chain binding proteins" by Rothman, J. E. *Cell* 59, 591-601 (1989), based on their ability to prevent the formation of wrong protein aggregates by binding to unfolded or partially denatured polypeptides. The heat-shock proteins of the hsp70 and hsp60 families are typical representatives of this heterogeneous group of components, as reviewed by Langer, T. & Neupert W. in *Curr. Topics in Microbiol. and Immun.* 167, 3-30 (1991); Pelham, H. R. B. *Nature* 332, 776-777 (1988); and Hartl, F.-U *Seminars in Immunolo* 3, in press (1991).

U.S. Ser. No. 07/261,573 filed Oct. 24, 1988, first described the folding function of hsp60, isolated from yeast mitochondria, and related proteins such as GroEL, isolated from *E. coli*. The essential function in protein folding of the members of the hsp60 family has since been demonstrated in vivo and in vitro. These so-called "chaperonins", described by Hemmingsen, S. M., et al., *Nature* 333, 330-334 (1988), include the groEL protein of *E. coli* and other bacteria, reviewed by Georgopoulos, C., et al., *J. Molec. Biol.* 76, 45-60 (1973); Stornborg, N. *J. molec. Biol.* 76, 25 44 (1973); Hendrix, R. W. *J. molec. Biol.* 129, 375-392 (1979); Bochkareva, E. S., et al., *Nature* 336, 254-257 (1988); Goloubinoff, P. et al., *Nature* 342, 884-889 (1989); Van Dyk, T. K., et al., *Nature* 342, 451-453; Lecker, S., et al. *EMBO J.* 8, 2703-2709 (1989); Laminet, A. A., et al., *EMBO J.* 9:2315-2319 (1990); Buchner J., et al. *Biochemistry* 30, 1586-1591 (1991), the rubisco binding-protein of chloroplasts, reviewed by Barraclough, R. & Ellis, R. J. *Biochim. Biophys. Acta* 608, 19-31 (1980); Musgrove, J. E., et al., *Eur. J. Biochem.* 163, 529-534 (1987); and Gatenby, A. A. & Ellis R. J. A. *Rev. Cell Biol.* 6, 125-149 (1990), and the mitochondrial hsp60, reviewed by McMullin, T. W. & Hallbert, R. L. *Molec. Cell. Biol.* 8, 371-380 (1988); Reading, D. S., et al., *Nature* 337-655-659 (1989); Cheng, M. Y., et al. *Nature* 337, 620-625 (1989); Ostermann, J., et al., *Nature* 341, 125-130 (1989); and Cheng, M. Y., et al., *Nature* 348, 455-458 (1990). They form tetradecameric complexes composed of two stacked 7mer rings of approximately 60,000 Dalton subunits that have ATPase activity.

GroEL and the mitochondrial hsp60 functionally cooperate with an additional component, groES, described by Chandrasekhar, G. N., et al., *J. Biol. Chem.* 261, 12414-12419 (1986); Lubben, T. H., et al., *Proc. Natl. Acad. Sci. U.S.A.* 87, 7683-7687 (1990); and Viitanen, P. V. et al. *Biochemistry* 29, 5665-5670 (1990), a ring-shaped complex of seven approximately 10,000 Dalton subunits which has been reported by Chandrasekhar and Viitanen to inhibit the ATPase activity of groEL. The groE proteins are required for lambda phage head-assembly. The rubisco binding-protein mediates the assembly of hexadecameric ribulose bisphosphate carboxylase (rubisco) in chloroplasts. The assembly of dimeric prokaryotic rubisco has been successfully reconstituted in vitro using purified groEL and groES by Goloubinoff, et al., and Viitanen, et al. Recently, the mitochondrial hsp60 has been shown to be necessary not only for the oligomeric assembly of proteins but also for the chain folding of monomeric polypeptides. However, the molecular mechanism of this ATP-driven process remaihs to be elucidated, and, as a result, how to use and manipulate this mechanism on a practical basis.

U.S. Ser. No. 07/721,974 entitled "Chaperonin-Mediated Protein Folding" filed Jun. 27, 1991 by Franz-Ulrich Hartl and Arthur L. Horwich, described the mechanisms and components required for chaperonin-dependent folding of proteins, as elucidated using the groEL and groES proteins of *E. coli* to reconstitute two monomeric enzymes, dihydrofolate reductase (DHFR) and rhodanese. While DHFR is able to fold spontaneously upon dilution from denaturant, this is not observed with rhodanese. The results demonstrated that GroEL, or its eukaryotic equivalent hsp60, stabilizes an early intermediate on the folding pathway which appears to be the equivalent to the folding state described as "molten globule"; ATP-dependent folding occurs at the surface of groEL via intermediate conformations which are progressively more compact but still enzymatically inactive; by regulating the groEL ATPase, groES, or its eukaryotic equivalent, accomplishes a critical folding step(s) at GroEL by modulating stepwise, ATP-dependent release of the protein substrate from the groEL scaffold. The folding reaction required Mg-ATP and the chaperonin proteins (provided in the preferred embodiment as 5 mM Mg acetate and 1 mM ATP), GroEL or hsp60, and GroES or eukaryotic equivalent.

Further utilization of the chaperonin components to protect and refold proteins under a variety of conditions would be enhanced by isolation and characterization of chaperonin-like molecules from different systems.

It is therefore an object of the present invention to provide a chaperonin-like molecule isolated from a thermophilic archaebacterium having similar function to groEL, hsp60 and RUBISCO-binding protein.

It is a further object of the present invention to provide a chaperonin-like molecule isolated from an archebacterial source which is homologous to an eukaryotic protein.

SUMMARY OF THE INVENTION

TF55 is a homooligomeric complex of two stacked rings, closely resembling the quaternary structure of the chaperonins, groEL, hsp60, and RUBISCO-binding protein. Instead of 7-member rings, however, most rings of TF55 contain 9 radially arranged members. The TF55 complex binds unfolded polypeptides in vitro, preventing aggregation at elevated temperature, and exhibits ATPase activity, features consistent with its function as a molecular chaperon. At the level of primary structure, TF55 is not significantly related to the chaperonins but is highly homologous (36–40% identity) to a ubiquitous eukaryotic protein, t complex polypeptide 1 (TCP1), which may have a similar role as a chaperone in eucaryotic cells.

BRIEF DESCRIPTION OF THE DRAWINGS

FIG. 2a, 2b and 2c demonstrate the interaction of TF55 and groEL with denatured proteins as analyzed by native gel electrophoresis, stained with Coomassie blue and fluorography after immunoblotting (FIG. 2a); graphed as percent of control of protein recovered on the native gel for groEL and TF55 alone and in combination with each other and Su9-DHFR, at 25° C., 56° C., 75° C., and 95° C.; and percent of control TF55 bound Su9-DHFR in the presence of BSA and ADH at 25° C., 56° C., and 70° C.

FIG. 2d is a 4–10% native gel containing E. coli proteins alone or with TF55, autoradiogram (lanes 1–4) or stained with Coomassie blue (lanes 6–10).

FIG. 2e is a graph of moles ATP hydrolysed/mole complexsec versus temperature (°C.) for groEL (squares) and TF55 (dark circles).

DETAILED DESCRIPTION OF THE INVENTION

Figure 1A:
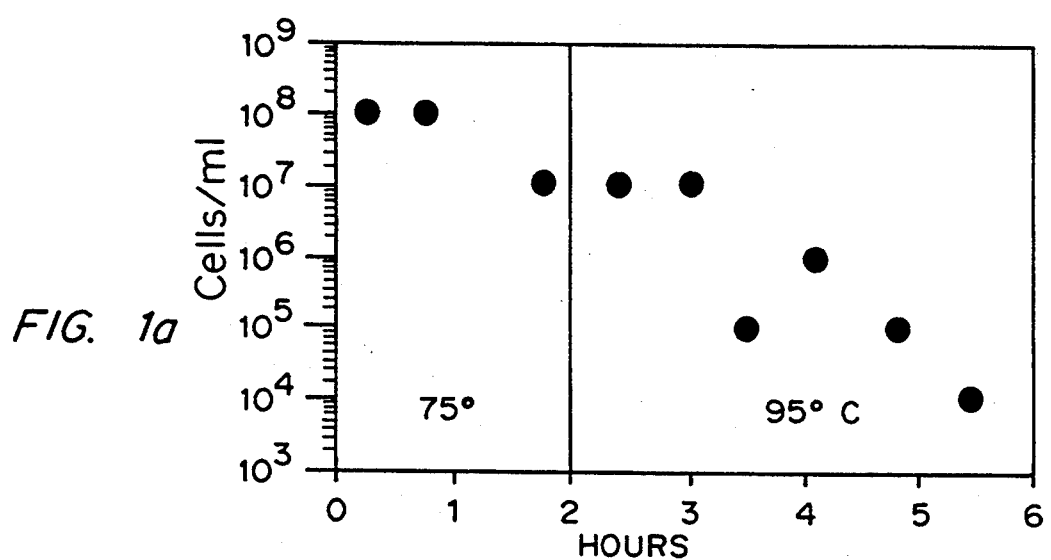
FIG. 1 is a graph of cells/ml versus hours at 75° C., 88° C., and 95° C.

Recent evidence suggests that components of archaebacteria are evolutionarily related to cognates in the eukaryotic cytosol. It has been determined that the major heat-shock protein of the thermophilic archaebacterium, Sulfolobus shibatae, is a molecular chaperone, homologous to an as yet unidentified chaperone component in the eukaryotic cytosol. Acquired thermotolerance in S. shibatae correlates with the predominant synthesis of this already-abundant protein, referred to as thermophilic 55 (TF55) by Trent, J. D., Osipiuk, J., & Pinkau, T. J. Bact. 172, 1478–1484 (1990). In Saccharomyces cerevisiae, TCP1 is an essential protein that may play a role in mitotic spindle formation, as reported by Ursic, D. & Culbertson, M. R. Mol. Cell. Biol. 11, 2629–2640 (1991). TF55 and TCP1 are believed to be members of a new class of molecules, unique at both the primary and quaternary structural levels, that function as molecular chaperones in archaebacteria and the eukaryotic cytosol.

Sulfolobus shibatae cells were radiolabeled for 15 min. at 75° C. or after shifting to 88° C., and total cell extracts were examined in SDS-PAGE. In contrast to the complex pattern observed at 75° C., a single radiolabeled protein with an apparent molecular weight of 55,000 (TF55) was detected at 88° C. Protein-staining indicated that this was the most abundant protein at all temperatures, and double-labeling experiments indicated that, under heat-shock conditions, its synthesis increased four to six-fold. The predominant synthesis of TF55 at 88° C. correlates with survival of the cells at an otherwise lethal temperature of 95° C., a response known as acquired thermotolerance. The acquisition of thermotolerance is generally associated with the induction of heat shock proteins. Therefore, TF55 was analyzed to see if it was related to any of the known heat shock proteins.

TF55 was purified from the soluble portion of Triton TM X-100 cell extracts by anion exchange chromatography and glycerol gradient sedimentation. Most of the TF55 sedimented in the gradient at 20S. By spectrophotometry, no nucleic acid was found in the 20S fraction. By SDS-PAGE, TF55 was the only protein detected in this fraction, suggesting it exists as a homooligomeric complex. A similar sedimentation behavior is exhibited by the chaperonins groEL, hsp60, and RUBISCO binding protein, which are 14mer complexes. When total soluble S. shibatae proteins were applied to a native polyacrylamide gel, TF55 was found near the top of the gel, migrating more slowly than the chaperonins, as reported by Musgrove, J. E., et al., Eur. J. Biochem. 163, 529–534 (1987), Ostermann, J., et al., Nature 341, 125–130 (1989), and Martin, J., et al., Nature 352, 36–42 (1991), and, instead of a single band, a pair of bands was detected. When these bands were excised and analyzed by SD§-PAGE, both appeared as 55 kDa proteins.

In scanning transmission electron microscopy (STEM), the TF55 complex usually appeared in negative stain as a nine-unit, radially symmetric ring with a dark core in one orientation (end view), and a two-fold symmetrical layered structure with connecting 'fingers' in the other (side view). In comparison, groEL had a similar double-ring structure, but with an apparently seven-fold symmetry on end view and a somewhat more flattened appearance on side view. While images of negatively stained TF55 complex showed that the majority of end views had nine-fold symmetry, some eight-fold symmetrical complexes were also observed. STEM diameter and mass determinations of unstained, freeze-dried specimens support the observation from native gels that there may be two size classes. Complexes of smaller radius (less than 12.1 nm) had masses of 930±50 kDa (N=32), while the larger ones had 1000±64 kDa (n=130), values that approximately correspond to a complex with 16-18 members. An eightfold symmetrical particle has recently been reported in another thermophilic organism, *Pyrodictium occultum*, formed of 55 and 59 kDa polypeptides, as described by Phipps, B. M., et al., *EMBO J.* 10, 1711–1722, (1991).

The ability of TF55 to bind unfolded proteins was assessed to test whether TF55 could function as a molecular chaperone. A sensitive binding assay was established using the L-[$^{35}$S]methionine-radiolabeled fusion protein Su9-DHFR, consisting of the first 69 residues of the mitochondrial precursor protein Fo-ATPase subunit 9 joined to the complete mouse dihydrofolate reductase, as described by Pfanner, N., et al., *Cell* 49, 815–823 (1987). (28). The protein was partially purified from a reticulocyte lysate and was unfolded in 6M guanidinium-Cl (GdmCl). Su9-DHFR aggregates upon dilution from the denaturant. Accordingly, when the fusion protein was diluted from GdmCl into buffer and the mixture applied to a native polyacrylamide gel, the protein failed to enter the gel. When diluted into a buffer containing TF55 complex, however, the radiolabeled product migrated at the same position as the complex. In a control experiment with purified groEL complex instead of TF55, the fusion protein migrated with the groEL complex. The TF55-bound protein was shown to be the DHFR fusion protein by excision from the native gel followed by SDS-PAGE. More than 50% of the added Su9-DHFR bound to TF55. Strikingly, the complex between denatured Su9-DHFR and TF55 formed at 25° C. proved to be heat stable up to 75° C. The TF55 complex itself became labile under our assay conditions above 80° C. In contrast, more than 60% of Su9-DHFR was lost from the groEL complex upon incubation at 56° C., even though the complex itself appeared to be intact at this temperature.

Next, whether the binding of Su9-DHFR to the TF55 complex could be prevented was tested by first incubating the complex with mesophilic or thermophilic proteins at high temperature. Incubating TF55 with a 6-fold molar excess of the mesophilic protein, bovine serum albumin (BSA), for 5 min. at 70° C. reduced its ability to bind Su9-DHFR at 25° C. by about 60%. This effect was dependent on TF55 being present during heat denaturation of BSA, however, and was not observed if TF55 was added after heat denaturation of BSA. This suggests that TF55 binds more effectively to proteins as they unfold, rather than to aggregates of already denatured proteins. Furthermore, incubating TF55 with a thermostable alcohol dehydrogenase (ADH) from Thermoanaerobium for 5 min. at 70° C. did not affect its capacity to subsequently bind Su9-DHFR, indicating that TF55 does not bind native proteins. Notably, neither BSA nor ADH were able to prevent the aggregation of Su9-DHFR diluted from 6M GdmCl in the absence of TF55.

A more general demonstration of the ability of TF55 to bind unfolded proteins employed total Triton ™- soluble *Escherichia coli* proteins labeled in vivo with L-[$^{35}$S]methionine. Binding these proteins in their native conformation at 23° C. was negligible. When they were heated to 70° C. in the presence of TF55, however, the binding increased substantially. This binding was much less pronounced when the *E. coli* proteins were incubated at 70° C. prior to the addition of TF55, corroborating the observation with BSA that the TF55 complex binds proteins as they become unfolded.

Because the binding and release of proteins from chaperones is associated with ATP hydrolysis, the purified TF55 complex was tested for ATPase activity. At a normal growth temperature for *S. shibatae* (75° C.), 0.45 moles ATP were hydrolyzed per mole complex per sec, a value similar to that reported for the ATPase activity of the groEL complex at the normal growth temperature of *E coli*. The upper limit of ATPase activity for both complexes correlates with the temperatures at which the complexes dissociate.

The primary structure of TF55, deduced from cloned genomic DNA, predicts a hydrophilic polypeptide of 552 amino acids (59,682 Da) (Seq. ID No. 2). This polypeptide bears a significant relationship along its entire length to a eukaryotic protein, t complex polypeptide 1 (TCP1) o It has 40% identity and 62% similarity to mouse TCP1 and 36% identity and 50% similarity to *S. cerevisiae* TCP1. Mouse TCP1 is abundantly expressed in developing sperm and has been implicated in the phenomenon of malespecific transmission ratio distortion. A more general function of TCP1, however, is suggested by its presence in all other mammalian cell types examined to date, in *Drosophila melanogaster,* and in *S. cerevisiae*. In *S. cerevisiae,* TCP1 is an essential gene, and a cold-sensitive mutation impairs mitotic spindle formation. Initial localization studies suggested that TCP1 was associated with membranes; however, more recent examination indicates that a substantial portion of the protein is soluble in the cytosol. A more general role for TCP1 has been suggested, based on its size and limited sequence homology to the bacterial chaperonins, as reported by Ahmad, S. & Gupta, R. S. *Biochim. Biophys. Acta* 1087, 253–255 (1990), and Ellis, J. R. *Science* 250, 954–959 (1990).

The sequences of TF55 (Seq. ID No. 1) and TCP1 were compared with both the hsp60 family (chaperonins) as well as the hsp70 family of chaperones. The parameters of the comparison confirmed the homology between TF55 and TCP1, but indicated no significant homology between either of these molecules and the chaperones tested. The results are shown in Table I.

TABLE I

| | TCP1 mouse | TCP1 yeast | groEL | hsp60 | hsp65 | hsp70 | dnaK |
|---|---|---|---|---|---|---|---|
| TF55 | 10.14 | 12.04 | 2.32 | 1.69 | 0.40 | 1.011 | 0.64 |
| TCP1 mouse | — | 37.85 | 1.45 | 2.25 | 2.30 | 1.56 | 0.84 |
| TCP1 yeast | | — | 0.84 | 2.30 | 1.57 | 1.00 | 1.78 |
| groEL | | | — | 33.74 | 38.80 | 0.64 | 0.39 |
| hsp60 | | | | — | 24.80 | 2.24 | 1.34 |
| hsp65 | | | | | — | −0.39 | −0.97 |

TABLE I-continued

| | | Sequence comparisons. | | | | |
|---|---|---|---|---|---|---|
| TCP1 mouse | TCP1 yeast | groEL | hsp60 | hsp65 | hsp70 | dnaK |
| hsp70 | | | | | — | 34.86 |

The computer program "Relate" (Protein Identification Resource; National Biomedical Research Foundation) was employed, using the Mutation Data Matrix and a segment length of 10 amino acids. Values are given in "Standard Deviation Units" (38). A value greater than 7 suggests a significant homology between sequences. Sources of sequences: TF55: FIG. 4a; TCP1b mouse: GENBANK M12899; TCP1 *S. cerevisiae*: GENBANK M21160; groEL *E. coli*: GENBANK S01432; hsp60 *S. cerevisiae*: GENBANK M33301; hsp65 *Mycobacterium tuberculosis* (39); hsp70 (SSA4) *S. cerevisiae*: GENBANK J05637; dnak *E. coli*; GENBANK K01298.

In summary, several lines of evidence suggest that the major heat shock protein of a thermophilic archaebacterium functions as a molecular chaperone: it binds unfolded proteins, it prevents their aggregation at high temperature, and it exhibits ATPase activity. Its quaternary structural similarity to the groEL complex, which is known to mediate polypeptide chain folding, suggests that TF55 may also be involved in de novo protein folding and assembly.

The striking similarity between the primary structures of TF55 and TCP1 suggests that these molecules carry out similar functions. The involvement of TCP1 in mitotic spindle formation in yeast and the recent evidence for a cytoskeleton in archaebacteria suggest that the two proteins may play a specialized role in cytoskeletal assembly. However, the predominant synthesis of TF55 during thermal stress and its ability to bind unfolded proteins in vitro suggest a more general chaperone function in the archaebacteria that could include protein folding.

As used herein, TF55 is any multimeric protein isolated from a thermophilic archaebacterium having at least 40% homology to the sequence encoding TF55 isolated from, or expressed from a gene isolated from, *S. shibatae*, exhibiting ATPase-dependent folding activity or binding to proteins to stabilize them and prevent denaturation or aggregation under denaturing conditions such as elevated temperatures. In the preferred embodiment, the TF55 is added to the protein to be stabilized prior to exposure of the protein to the denaturing conditions or prior to refolding. The purified TF55 can either be added to the system in which the protein to be properly folded (either as it is synthesized, prior to or after chemical or heat denaturation) is present, or the genes encoding the relevant protein(s) expressed in the cell culture system in which the protein to be properly folded is being expressed. In the preferred embodiment, the gene for the TF55 is introduced into the cell culture system using an appropriate vector. Such vectors are commercially available, for example, from BioRad Laboratories, Richmond, Calif. or from International Biotechnologies, Inc., either for expression of proteins in procaryotic or eukaryotic cell culture. The gene to be expressed is inserted into the vector and the cells in which the gene is to be expressed as described by the supplier. Suitable cell culture systems include *E. coli*, yeast such as *S. cerevisae*, and mammalian cells such as CHO cells, all available from a variety of sources, including the American Type Culture Collection of Rockville, Md. For folding to occur, it is expected that at least one additional cooperating component present in the thermophilic archaebacteria, analogous to the groEL and groES system in *E. coli*, will have to be present, along with Mg-ATP.

The following methods and data were used to reach these conclusions. The teachings of cited references are specifically incorporated herein.

EXAMPLE 1: Synthesis of TF55 and acquisition of thermotolerance

Figure 1B:
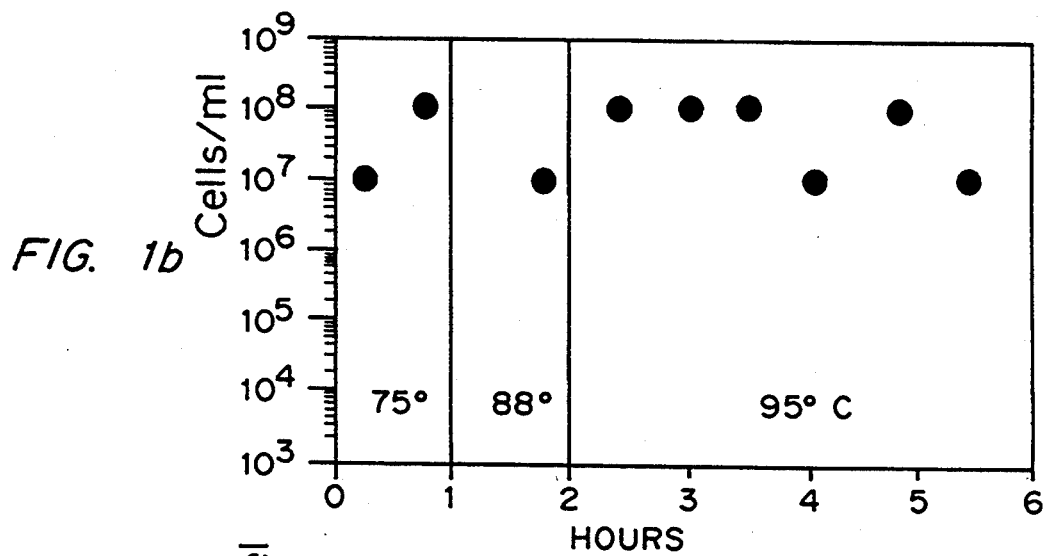

Synthesis of TF55 predominates at near-lethal temperature (88° C.). Cells grown at 75° C. in Brock's salts and 0.2% Dextrin, as described by Trent, J. D., Osipiuk, J., & Pinkau, T. *J. Bact.* 172, 1478–1484 (1990), were pulse-radiolabeled for 15 min., either at 75° C. or 15 min. after shifting to 88° C., by addition of L-[$^{35}$S]methionine (800 Ci/mmol, Amersham), 10 μCi/ml. The cells were harvested at 4° C., washed with water, then solubilized in SDS-sample buffer (3% (w/v) SDS, 5% (v/v) β-mercaptoethanol, 10% glycerol, 65 mM Tris-Cl pH 6.8, 0.001% (w/v) bromophenol blue) and analyzed by SDS-10% PAGE. The Coomassie-stained gel was dried and autoradiographed. The rate of TF55 synthesis at various temperatures was quantified using a double-labeling technique reported by Pedersen, S., et al., *Mol. Gen. Genet.* 144, 339–343 (1976). Cells radiolabeled at 75° C. for 30 min. with L-[$^3$H]leucine (50 Ci/mmol), Amersham), 25 μCi/ml, were chased with a greater than 3000-fold molar excess (3 mM) L-leucine, then pulse radiolabeled for 10 min. with L-[$^{35}$S]methionine, 10 μCi/ml, after shifting to various temperatures. Cells were harvested and analyzed by SDS-PAGE as above. Bands corresponding to TF55 were excised from dried gels and $^3$H and $^{35}$S were determined by scintillation counting with non-overlapping windows. Controls that were not radiolabeled with $^{35}$S indicated that the amount of $^3$H labeling did not vary with temperature. The relative increase of the rate of TF55 synthesis was determined by comparing the ratio of $^{35}$S to $^3$H at 88° with the ratio at 75° C.;

Cells from a 75° C. culture were shifted directly to 95° C. (as shown in FIG. 1-I) or to 88° C. for 1 hr. and then to 95° C. (as shown in FIG. 1-II). The concentration of viable cells was determined by a most-probable-number dilution procedure as previously described by Pedersen, S., et al., *Mol. Gen. Genet.* 144, 339–343 (1976).

EXAMPLE 2: Purified TF55 is a homooligomeric double ring complex

TF55 sediments at 20S in glycerol gradient centrifugation; TF55 migrates similarly to the chaperonin 14mer complexes in a native polyacrylamide gel; and TF55 appears as a stacked ring complex in scanning transmission electron microscopy (STEM).

*S. shibatae* CELLS GROWN AT 75° C. were collected, washed, resuspended in a buffer containing 50 mM Hepes, pH 7.5 and 5 mM MgCl$_2$, and lysed at 4° C. by addition of Triton ™ X100 to a final concentration of 0.1% (v/v). The lysate was diluted with the buffer to 0.01% (v/v) Triton ™ X100 and centrifuged at 100,000 ×g for 1 hr. The supernatant was analyzed in a 4–10% acrylamide native gel, as described in Musgrove, J. E., et al., *Eur. J. Biochem.* 163, 529–534 (1987), or, for TF55 purification, was subjected to Q-Sepharose fast flow (Pharmacia) FPLC anion exchange chromatography. TF55-containing chromatographic fractions, eluted at 150–200 mM NaCl, were concentrated by ultrafiltration (Centricoh ™ 30, Amicon) and further fractionated by sedimentation in a 10–30% (v/v) glycerol gradient centrifuged at 25,000 rpm for 20 hr. at 4° C. in an SW27 rotor (Beckman).

Samples of each fraction from the glycerol gradient were solubilized in SDS sample buffer and analyzed by SDS-PAGE. Identical samples were separated in a native gel and one lane was stained with Coomassie, while the other was immunoblotted using the method described by Ostermann, J., et al., *Nature* 341, 125–130 (1989). Coomassie-stained proteins were excised from the dried native gel, placed in the wells of a 10% polyacrylamide SDS gel, and rehydrated by overlaying with 1M Tris-Cl, pH 8.0, for 60 min. The Tris was replaced with SDS sample buffer and electrophoresis was carried out. For scanning transmission electron microscopy, 2.5 µl of a 100 µg/ml solution of either TF55 from the 20S glycerol gradient fraction or purified groEL complex, prepared as described in Viitanen, P. V., et al., *Biochemistry* 29, 5665–5671 (1990), was injected into a 2.5 µl drop of 10 mM Hepes buffer (pH 7.0) on a 2 nm thick carbon substrate supported by a holey carbon film on a titanium grid. After several washes with 20 mM ammonium acetate, the samples were either stained with 2% (w/v) uranyl acetate, blotted, and air-dried, or blotted with filter paper, plunged into liquid nitrogen slush, and freeze-dried overnight in an ion-pumped chamber. All specimens were transferred to the microscope under vacuum and observed at −150° C. with minimal dose techniques. Scattered electron counts were recorded digitally as the 0.25 nm probe (40 keV) scanned the specimen in a 512×512 raster. Mass measurements on the unstained, freeze-dried specimens were carried out as described by Wall, J. S. & Hainfeld, J. F. *Ann. Rev. Biophys. Biophys. Chem.* 15, 355–376 (1986), using tobacco mosaic virus (TMV) as an internal mass standard. Particles for mass analysis were selected on the basis of separation from neighbors, clean surrounding background, sharp edges, and lack of obvious defects.

EXAMPLE 3: Interaction of TF55 and groEL with denatured proteins analyzed by native gel electrophoresis, and the ATPase activity of TF55 and groEL Binding of GdmCl-denatured Su9-DHFR, stability of binding of Su9-DHFR over a range of temperatures, influence of heat-denatured bovine serum albumin (BSA) and of thermostable alcohol dehydrogenase (ADH) on binding of Su9-DHFR, binding of *E. coli* proteins, and ATPase activity at increasing temperatures were determined. The results are shown in FIGS. 2a and 2b.

Su9-DHFR fusion protein (residues 1–69 of the precursor of Neurospora Fo-ATPase subunit 9 joined to complete mouse dihydrofolate reductase by three linker residues, described by Pfanner, N., et al., *Cell* 49, 815–823 (1987)) was synthesized in a reticulocyte lysate in the presence of L-[$^{35}$S]methionine (Amersham). The radiolabeled protein was precipitated by addition of ammonium sulfate to 66% saturation and the precipitate was dissolved in 2 volumes (compared to original lysate) of 6M guanidinum-Cl (GdmCl), 2 mM dithiothreitol (DTT), 30 mM Tris.Cl, pH 7.5. 1 µl of GdmCl-denatured Su9-DHFR was added at 25° C. to 49 µl of 50 mM KCl, 2 mM DTT, 30 mM Tris-Cl, pH 7.5 containing 4 µg of either purified TF55 or groEL (FIG. 2a, lanes 1,4 and 2,5). In one reaction, TF55 and groEL were omitted (lane 3). After addition of 5 µl of gel loading solution (40% v/v glycerol, 0.004% (w/v) bromophenol blue)), the binding reactions were separated on 3–15% native polyacrylamide gels, as described by Martin J., et al., *Nature* 352, 36–42 (1991). The Coomassie-stained gel was analyzed by fluorography (lanes 3–5). The TF55-containing band was excised from the dried native gel, inserted into the well of an SDS-polyacrylamide gel, and subjected to SDS-PAGE. Su9-DHFR alone was analyzed as a standard (lane 6). A fluorograph of the SDS gel is shown (lane 7). Binding of Su9-DHFR was carried out at 25° C. as above. The reactions were then incubated for 5 min. at the indicated temperatures. After cooling to 25° C., analysis by native gel electrophoresis and fluorography was performed.

Figure 2B:
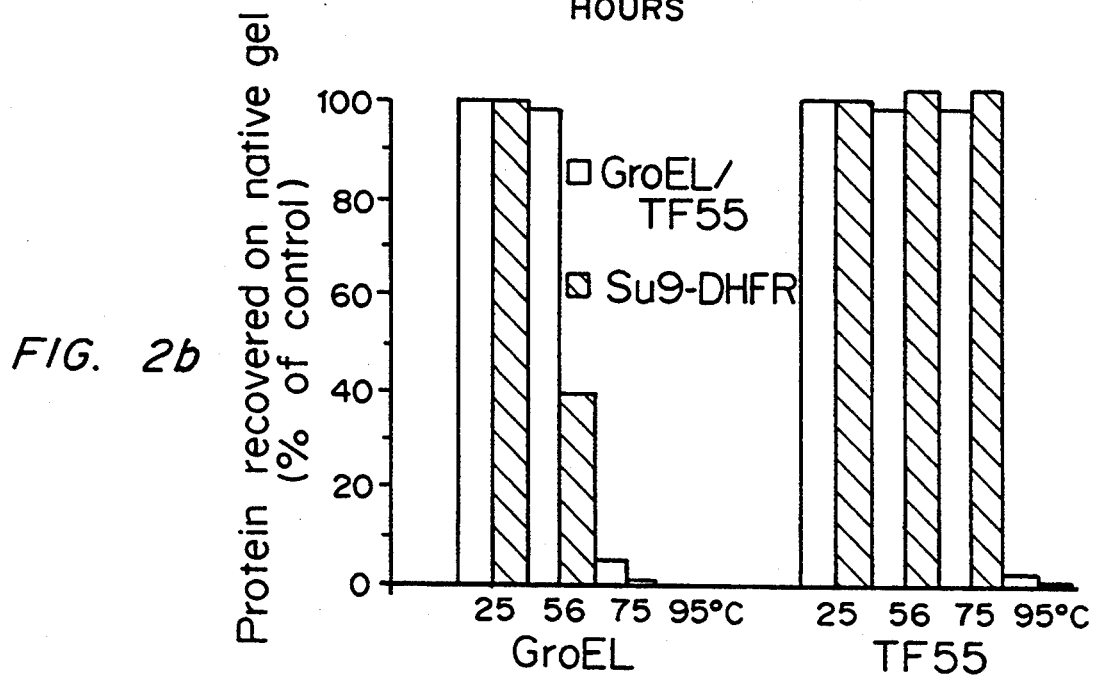
FIGS. 2a-e are the results of the characterization of the isolated TF55: a) binding of GdmCl-denatured Su9-DHFR; b) stability of binding of Su9-DHFR over a range of temperatures; c), influence of heat-denatured bovine serum albumin (BSA) and of thermostable alcohol dehydrogenase (ADH) on binding of Su9-DHFR; d) binding of E. coli proteins; and e) ATPase activity at increasing temperatures.
Figure 2A:
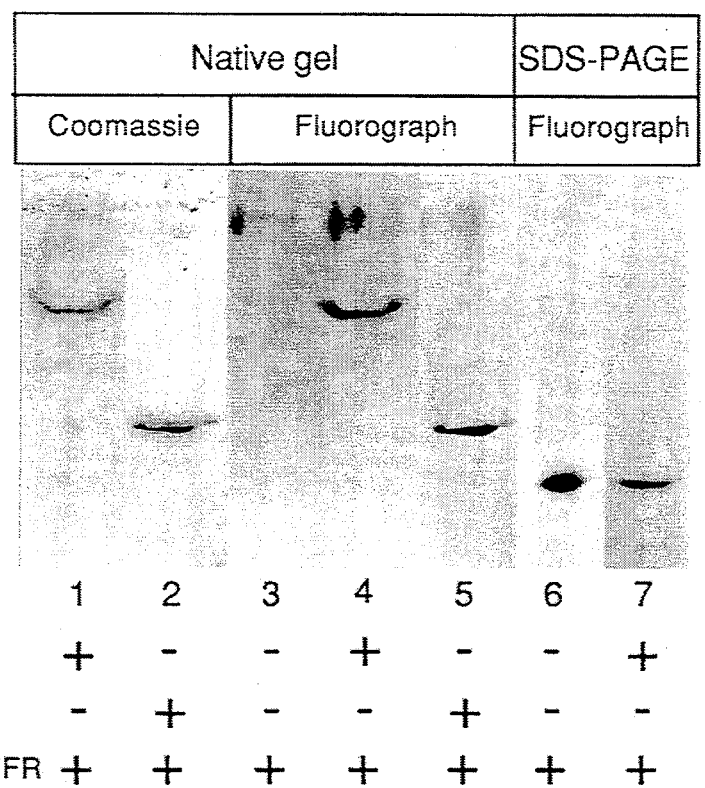

As shown in FIG. 2b, the amount of GroEL and TF55 (open bars), as well as bound Su9-DHFR (hatched bars), were quantified by laser densitometry and are expressed as percent of the amounts recovered after incubation at 25° C.

Figure 2C:
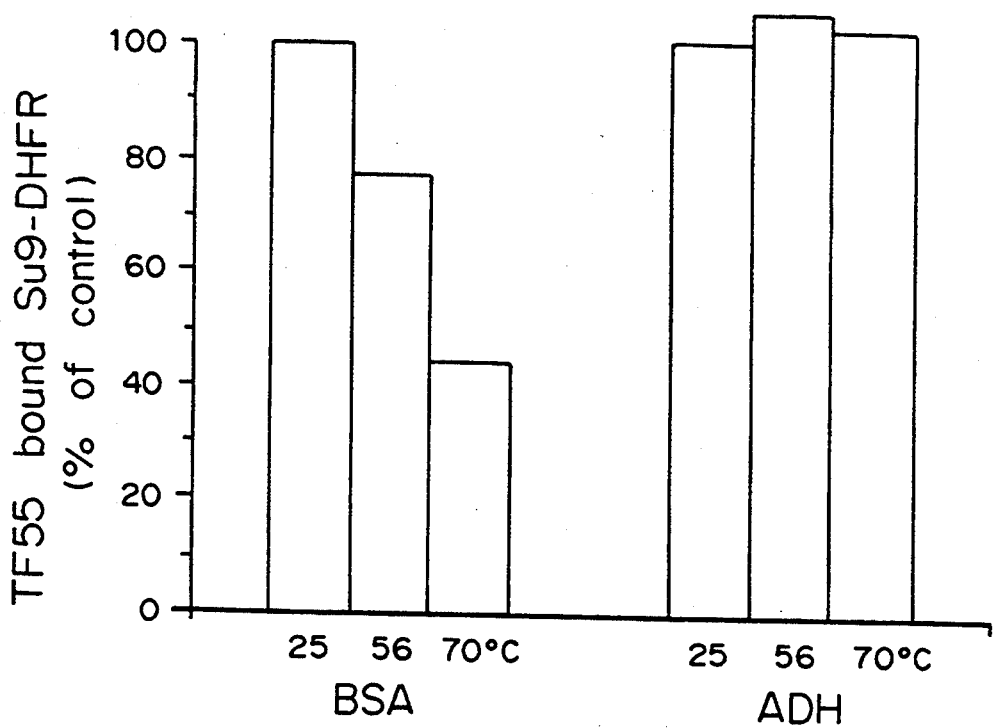

As shown in FIG. 2c, reactions containing 4 µg TF55 were incubated for 5 min at 25, 56, or 70° C. in the presence or absence of 25 pmole of fatty acid-free bovine serum albumin (BSA, Sigma) or of alcohol dehydrogenase from *Thermoanaerobium brockii* (ADH, Sigma). After cooling to 25° C., Su9-DHFR was added and binding was analyzed as in 'b'. In control reactions, BSA or ADH was incubated at the respective temperatures in the absence of TF55. Then TF55 and Su9-DHFR were added at 25° C. Amounts of TF55-bound Su9-DHFR are expressed as percent of protein bound in the corresponding control reaction. The absolute amounts of Su9-DHFR bound in control reactions were equal to those measured in the absence of BSA or ADH irrespective of the temperature during the initial incubation.

Figure 2E:
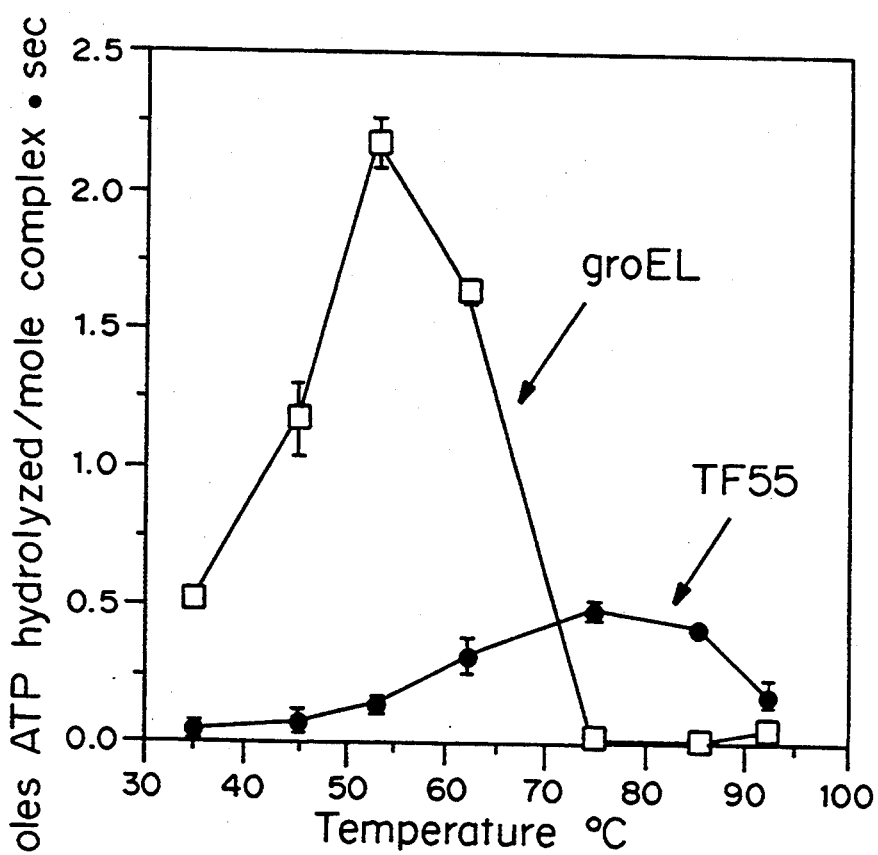
Figure 2D:
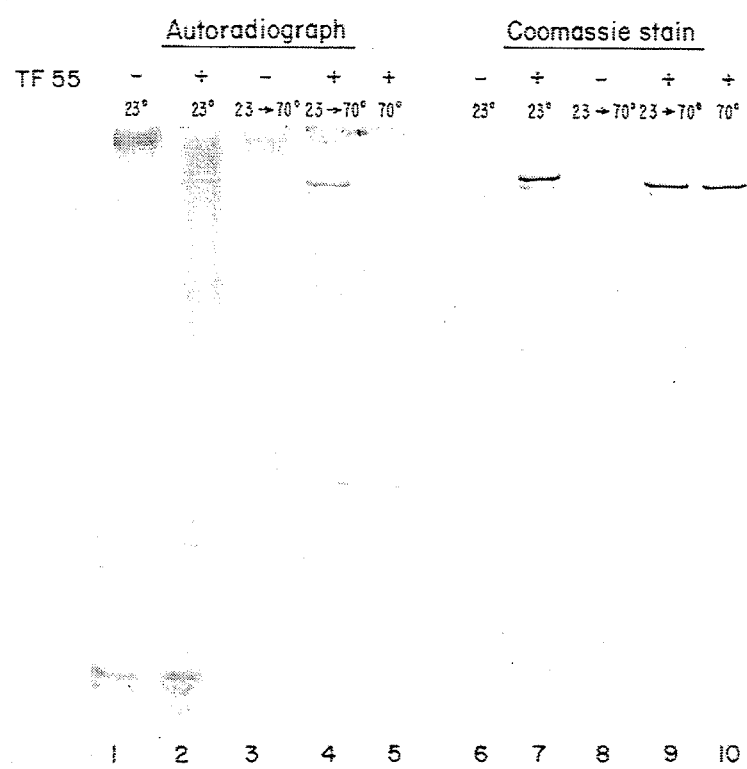

As shown in FIG. 2d, radiolabeled *E. coli* proteins were prepared by addition of 1 mCi L-[$^{35}$S]methionine (800 Ci/mmol, Amersham) to a 1 ml log phase culture growing at 37° C., for 20 min. Cells were harvested by centrifugation, lysed at 4° C. in 25% sucrose, 50 mM Tris-Cl, pH 7.5 by addition of lysozyme to 2 mg/ml, followed by addition of 4 volumes of 50 mM Hepes, pH 7.4, 0.05% Triton X100. The lysate was centrifuged at 15,000 ×g for 20 min. and the supernatant collected. 2 µg of soluble *E. coli* protein (12,500 cpm TCA-precipitable $^{35}$S-labeled proteins) was mixed with 8 µg purified TF55 in 50 mM Hepes buffer, pH 7.4 (+), or with Hepes buffer alone (−), (final volume 50 µl). Following incubation, samples were cooled briefly on ice, native gel loading buffer (final conc: 10% (v/v) glycerol, 0.001% (w/v) bromophenol blue) was added, and the samples were immediately applied to a 4–10% native gel. The native gel was Coomassie stained, dried, and autoradiographed. Lanes 1–5, autoradiogram showing the migration of radiolabeled *E. coli* proteins. Lanes 6–10, Coomassie staining pattern, showing migration of TF55 complex. Lanes 2,7, incubation with TF55 for 15 min at 23° C.; lanes 1,6, minus TF55. Lanes 4,9, incubation with TF55 for 15 min at 23° C., then incubation at 70° C. for 15 min; lanes 3,8, minus TF55. Lanes 5,10, incubation of E. coli extract for 5 min at 70° C., then addition of TF55 for additional 15 min.

As shown in FIG. 2e, for assay of ATPase activity samples containing 8 μg TF55 complex or groEL complex in 99 μl of 50 mM Hepes, 5 mM MgCl$_2$, 5 mM KCl, were equilibrated at the assay temperature for 5 min. before adding 1 μl 100 mM ATP. After 30 min, orthophosphate was measured by the Malachite-green method reported by Lill, R., et al., Cell 60, 271–280 (1990). Values, corrected for sample orthophosphate and spontaneous ATP hydrolysis, are a mean±SD for three separate experiments.

The nucleotide (from 5' to 3' end) and predicted amino acid sequences of the S. shibatae TF55 gene are as follows.

The nucleotide sequence including the promoter is
CATATTTTCGATAACTCACGAAGAAAGT-GATCGGATCTGATTTGAGCAAAATTTT TATAACCTTT TTTTAAGACAGAGT-GGAAGGTGCGTAAA The nucleotide sequence (Seq. ID No. 1) encoding the protein is

```
ATG GCA ACA GCT ACA GTT GCA ACT ACA CCC GAA GGT ATA CCT GTA ATA
ATT TTA AAA GAG GGA TCA AGT AGA ACA TAT GGA AAA GAA GCT TTA AGG
GCT AAT ATT GCT GCA GTG AAA GCA ATT GAA GAG GCA TTA AAA AGC ACC
TAT GGT CCA CGT GGA ATG GAT AAG ATG TTC GTT GAT AGC TTA GGA GAT
ATT ACA ATA ACA AAT GAT GGA GCC ACT ATT CTT GAT AAA ATG GAT TTA
CAA CAC CCA ACA GGT AAG CTT TTA GTT CAG ATA GCT AAA GGA CAA GAC
GAG GAA ACA GCT GAT GGC ACT AAA ACT GCT GTA ATT CTT GCT GGA GAA
TTA GCT AAA AAA GCA GAA GAT CTT TTA TAT AAG GAG ATT CAC CCA ACA
ATA ATT GTA AGC GGA TAT AAG AAG GCA GAA GAA ATT GCA TTA AAG ACC
ATC CAA GAT ATA GCA CAA CCG GTC AGC ATA AAT GAT ACT GAC GTA CTT
AGG AAA GTA GCA TTA ACA TCC TTA GGC AGT AAG GCA GTA GCA GGC GCA
CGA GAG TAT TTA GCT GAC CTT GTG GTT AAA GCA GTG GCA CAA GTA GCA
GAA TTA AGA GGA GAT AAG TGG TAT GTT GAT CTA GAT AAT GTA CAA ATA
GTT AAA AAA CAT GGT AGC ATT AAT GAT ACT CAA TTA GTA TAC GGC
ATA GTA GTT GAT AAG GAA GTT GTA CAT CCG GGC ATG CCA AAG AGG ATT
GAA AAT GCT AAG ATA GCC CTT TTA GAC GCT TCA TTA GAA GTT GAG AAA
CCC GAA TTG GAT GCA GAA ATA AGA ATT AAC GAT CCA ACA CAG ATG CAC
AAA TTC TTG GAA GAA GAA ATA TTG AAA GAA AAA GTA GAT AAG
ATT GCA GCT ACT GGT GCT AAC GTT GTA ATA TGC CAG AAA GGT ATC GAT
GAA GTT GCA CAA CAC TAT TTA GCT AAG AAA GGT ATA TTA GCT GTT AGG
AGA GCC AAG AAG AGT GAT TTA GAG AAA TTA GCT AGA GCT ACC GGA GGT
AGA GTC ATA TCA AAT ATT GAT GAA TTA ACT TCA CAA GAT CTA GGT TAT
GCC GCA TTA GTG GAA GAG AGA AAA GTA GGA GAG GAT AAG ATG GTA TTC
GTA GAA GGT GCA AAG AAT CCA AAA TCA GTT AGT ATA CTA ATA AGA GGA
GGA TTA GAG AGA GTA GTA GAT GAG ACT GAA AGA GCT CTT AGG GAC GCT
TTA GGT ACA GTG GCA GAT GTA ATA AGG GAT GGT AGA GCA GTA GCT GGT
GGT GGA GCT GTT GAG ATA GCT AAG AGA TTA AGA AAG TAT GCC
CCA CAA GTT GGT GGT AAA GAG CAA TTA GCA ATT GAA GCA TAT GCT AAT
GCA ATA GAA GGA CTT ATC ATG ATA TTG GCG GAA AAC GCA GGA TTA GAT
CCT ATA GAC AAA TTA ATG CAA TTA AGA AGT CTT CAC GAC AAT GAG ACC
AAT AAA TGG TAT GGA CTT AAT TTA TTT ACT GGA AAT CCA GAG GAT ATG
TGG AAA TTA GGT GTT ATT GAA CCG GCA CTA GTG AAA ATG AAT GCA ATT
AAG GCT GCA ACA GAA GCA GTA ACA TTA GTG TTA AGA ATA GAT GAT ATT
GTA GCA GCT GGA AAG AAG GGT GGA AGT GAG CCA GGC GGT AAG AAA GAG
AAA GAA GAA AAG TCC TCT GAA GAC
```

The predicted amino acid sequence (Seq. ID No. 2) is:

```
Met Ala Thr Ala Thr Val Ala Thr Thr Pro Glu Gly Ile Pro Val Ile
Ile Leu Lys Glu Gly Ser Ser Arg Thr Tyr Gly Lys Glu Ala Leu Arg
Ala Asn Ile Ala Ala Val Lys Ala Ile Glu Glu Ala Leu Lys Ser Thr
Tyr Gly Pro Arg Gly Met Asp Lys Met Phe Val Asp Ser Leu Gly Asp
Ile Thr Ile Thr Asn Asp Gly Ala Thr Ile Leu Asp Lys Met Asp Leu
Gln His Pro Thr Gly Lys Leu Leu Val Gln Ile Ala Lys Gly Gln Asp
Glu Glu Thr Ala Asp Gly Thr Lys Thr Ala Val Ile Leu Ala Gly Glu
Leu Ala Lys Lys Ala Glu Asp Leu Leu Tyr Lys Glu Ile His Pro Thr
Ile Ile Val Ser Gly Tyr Lys Lys Ala Glu Glu Ile Ala Leu Lys Thr
Ile Gln Asp Ile Ala Gln Pro Val Ser Ile Asn Asp Thr Asp Val Leu
Arg Lys Val Ala Leu Thr Ser Leu Gly Ser Lys Ala Val Ala Gly Ala
Arg Glu Tyr Leu Ala Asp Leu Val Val Lys Ala Val Ala Gln Val Ala
Glu Leu Arg Gly Asp Lys Trp Tyr Val Asp Leu Asp Asn Val Gln Ile
Val Lys Lys His Gly Gly Ser Ile Asn Asp Thr Gln Leu Val Tyr Gly
Ile Val Val Asp Lys Glu Val Val His Pro Gly Met Pro Lys Arg Ile
Glu Asn Ala Lys Ile Ala Leu Leu Asp Ala Ser Leu Glu Val Glu Lys
Pro Glu Leu Asp Ala Glu Ile Arg Ile Asn Asp Pro Thr Gln Met His
Lys Phe Leu Glu Glu Glu Asn Ile Leu Lys Glu Lys Val Asp Lys
Ile Ala Ala Thr Gly Ala Asn Val Val Ile Cys Gln Lys Gly Ile Asp
Glu Val Ala Gln His Tyr Leu Ala Lys Lys Gly Ile Leu Ala Val Arg
Arg Ala Lys Lys Ser Asp Leu Glu Lys Leu Ala Arg Ala Thr Gly Gly
Arg Val Ile Ser Asn Ile Asp Glu Leu Thr Ser Gln Asp Leu Gly Tyr
Ala Ala Leu Val Glu Glu Arg Lys Val Gly Glu Asp Lys Met Val Phe
Val Glu Gly Ala Lys Asn Pro Lys Ser Val Ser Ile Leu Ile Arg Gly
Gly Leu Glu Arg Val Val Asp Glu Thr Glu Arg Ala Leu Arg Asp Ala
Leu Gly Thr Val Ala Asp Val Ile Arg Asp Gly Arg Ala Val Ala Gly
Gly Gly Ala Val Glu Ile Glu Ile Ala Lys Arg Leu Arg Lys Tyr Ala
Pro Gln Val Gly Gly Lys Glu Gln Leu Ala Ile Glu Ala Tyr Ala Asn
```

-continued

| | | | | | | | | | | | | | |
|---|---|---|---|---|---|---|---|---|---|---|---|---|---|
| Ala | Ile | Glu | Gly | Leu | Ile | Met | Ile | Leu | Ala | Glu | Asn | Ala | Gly | Leu | Asp |
| Pro | Ile | Asp | Lys | Leu | Met | Gln | Leu | Arg | Ser | Leu | His | Glu | Asn | Glu | Thr |
| Asn | Lys | Trp | Tyr | Gly | Leu | Asn | Leu | Phe | Thr | Gly | Asn | Pro | Glu | Asp | Met |
| Trp | Lys | Leu | Gly | Val | Ile | Glu | Pro | Ala | Leu | Val | Lys | Met | Asn | Ala | Ile |
| Lys | Ala | Ala | Thr | Glu | Ala | Val | Thr | Leu | Val | Leu | Arg | Ile | Asp | Asp | Ile |
| Val | Ala | Ala | Gly | Lys | Lys | Gly | Gly | Ser | Glu | Pro | Gly | Gly | Lys | Lys | Glu |
| Lys | Glu | Glu | Lys | Ser | Ser | Glu | Asp |

Figure 3A:
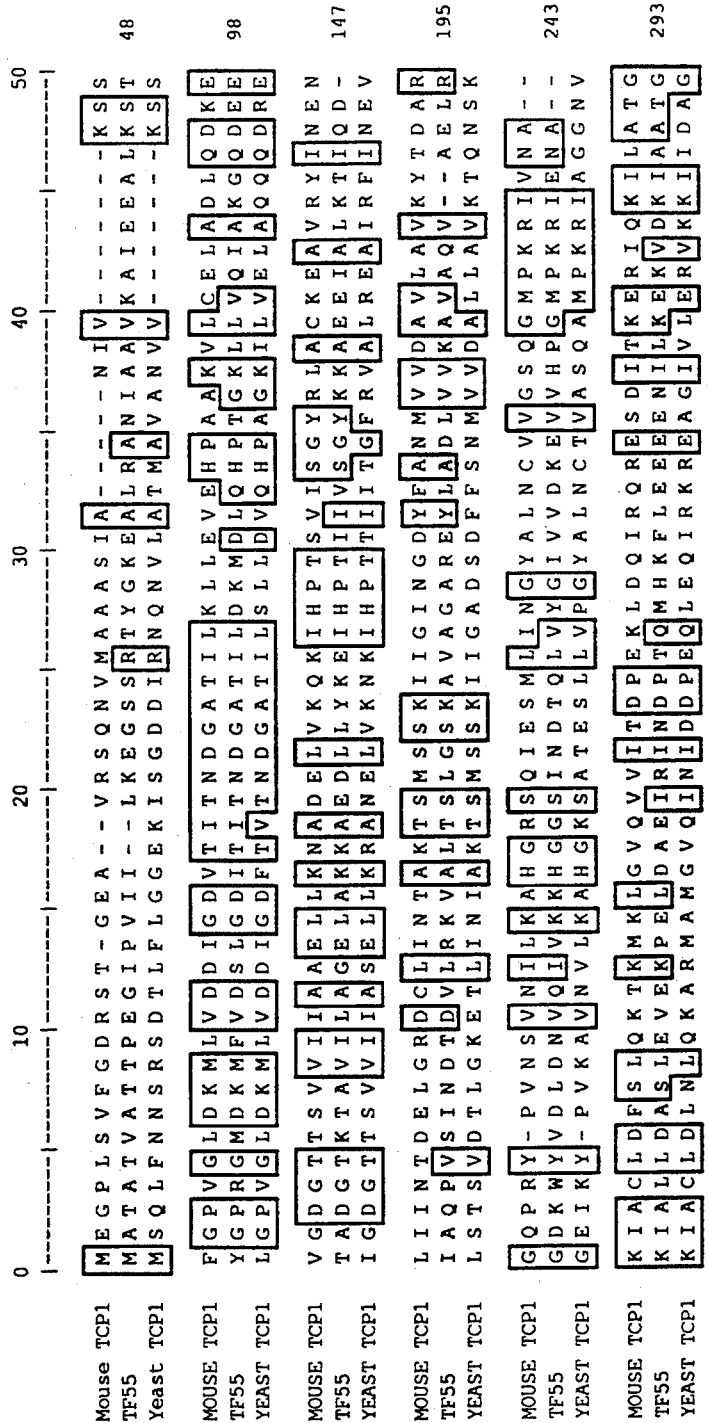
FIG. 3 is a comparison of the predicted amino acid sequence of the TF55 gene with eukaryotic TCP1 (mouse) and with TCP1 from S. cerevisiae.
Figure 3B:
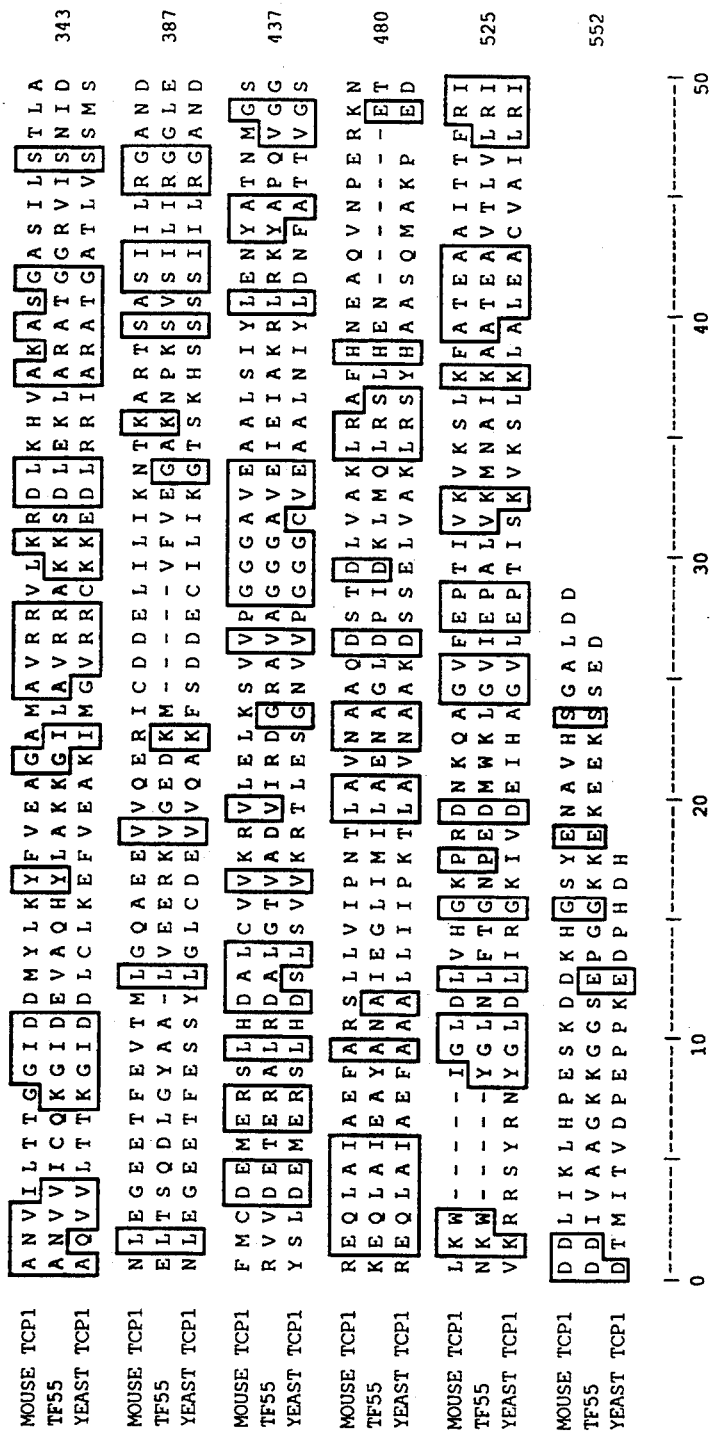

A comparison of the predicted amino acid sequence (Seq. ID No. 2) of the TF55 gene with eukaryotic TCP1 (mouse) and with TCP1 from *S. cerevisiae* is shown in FIG. 3. TF55 protein from cells grown at 88° C. was excised from a SDS polyacrylamide gel and cleaved with trypsin; the peptides were separated by HPLC on a C18 column. The amino acid sequence of two peptides was determined by sequential Edman degradation (peptide 1 corresponds to aa 514–524; peptide 2 corresponds to aa 338–359). Degenerate PCR primers (23-mers) were constructed, incorporating inosine at 4-base degenerate positions, corresponding to amino acids 1–9 of peptide 1 and amino acids 12–20 of peptide 2. Because the order of the two peptides in TF55 was then unknown, both coding and noncoding strands were synthesized. One of the pairs of primers produced a 520 base pair product when PCR amplification of genomic *S. shibatae* DNA was carried out (30 cycles, 95° C. ×2 min., 37° C. ×2 min., 67° C. ×2 min.). No product was observed with the other pair of primers. The PCR product was cloned in pBluescript ™ (Stratagene). DNA sequence analysis predicted the remaining three residues of peptide two, not represented in the PCR primer, as well as an additional tryptic peptide that had been previously sequenced (corresponding to aa 475–482). The cloned segment was used to screen two libraries constructed from *S. shibatae* genomic DNA digested either with Pst I or Xba I. Two overlapping clones were sequenced to produce the sequence shown above. The canonical promoter element of *S. shibatae*, TTTATA, reported by Reitner, W-D., et al., *Proc. Natl. Acad. Sci. U.S.A.* 87, 9509–9513 (1990), is underlined. Nucleotides are numbered in the left margin and amino acids in the right margin, in both cases from the translational start. The 55kDa protein recovered from SDS-PAGE and predicted by the DNA sequence was confirmed to be identical to that from the purified complex by the precise match of the amino acid sequence determined by sequential Edman degradation of several tryptic peptides prepared from the purified complex with the amino acid sequence predicted by the DNA sequence.

A 3-way comparison of sequences (TF55; TCP1b mouse: GENBANK M12899; TCP1 *S. cerevisiae*: GENBANK M21160) was carried out by the computer program THREEalign 2.0. The results are shown in FIG. 3.

Modifications and variations of the present invention, a chaperonin protein useful in assisting in proper folding of proteins, and method of use thereof, will be obvious to those skilled in the art. Such modifications and variations are intended to come within the scope of the appended claims.

We claim.

1. A method for preventing denaturation or aggregation of proteins exposed to denaturing or aggregating conditions comprising combining the protein to be prevented from denaturation or aggregation with a chaperone protein system comprising a preventing protein TF55, as isolated from a thermophilic archaebacterium and having at least 40% identity to the sequence encoding TF55 isolated from a gene isolated from *Sufolobus shitatae*.

2. The method of claim 1 wherein the preventing protein is TF55 isolated from *Sulfolobus shibatae*.

3. The method of claim 1 wherein the preventing protein is TF55 and is encoded by the nucleotide sequence shown in SEQ ID NO: 1.

4. The method of claim 3 wherein the preventing protein has the amino acid sequence shown in SEQ ID NO: 2.

5. The method of claim 1 wherein the protein to be prevented from denaturation or aggregation is bound by the preventing protein as the protein to be prevented from denaturation or aggregation is being synthesized.

6. The method of claim 1 wherein the protein to be prevented from denaturation or aggregation is bound by the preventing protein prior to exposure to conditions which would otherwise denature the protein to be prevented from denaturation or aggregation but not the preventing protein.

7. The method of claim 1 wherein the protein to be prevented from denaturation or aggregation is bound by the preventing protein prior to exposure to conditions which would otherwise cause aggregation of the protein to be prevented from denaturation or aggregation.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1749 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Sulfolobus shibatae ( i x ) FEATURE:
        ( A ) NAME/KEY: promoter
        ( B ) LOCATION: 1..93

( x i ) SEQUENCE DESCRIPTION: SEQ ID NO:1:

```
CATATTTTCG ATAACTCACG AAGAAAGTGA TCGGATCTGA TTTGAGCAAA ATTTTTATAA        60

CCTTTTTTTA AGACAGAGTG GAAGGTGCGT AAAATGGCAA CAGCTACAGT TGCAACTACA       120

CCCGAAGGTA TACCTGTAAT AATTTTAAAA GAGGGATCAA GTAGAACATA TGGAAAAGAA       180
```

| | | | | | |
|---|---|---|---|---|---|
| GCTTTAAGGG | CTAATATTGC | TGCAGTGAAA | GCAATTGAAG | AGGCATTAAA | AAGCACCTAT | 240
| GGTCCACGTG | GAATGGATAA | GATGTTCGTT | GATAGCTTAG | GAGATATTAC | AATAACAAAT | 300
| GATGGAGCCA | CTATTCTTGA | TAAAATGGAT | TTACAACACC | CAACAGGTAA | GCTTTTAGTT | 360
| CAGATAGCTA | AAGGACAAGA | CGAGGAAACA | GCTGATGGCA | CTAAAACTGC | TGTAATTCTT | 420
| GCTGGAGAAT | TAGCTAAAAA | AGCAGAAGAT | CTTTTATATA | AGGAGATTCA | CCCAACAATA | 480
| ATTGTAAGCG | GATATAAGAA | GGCAGAAGAA | ATTGCATTAA | AGACCATCCA | AGATATAGCA | 540
| CAACCGGTCA | GCATAAATGA | TACTGACGTA | CTTAGGAAAG | TAGCATTAAC | ATCCTTAGGC | 600
| AGTAAGGCAG | TAGCAGGCGC | ACGAGAGTAT | TTAGCTGACC | TTGTGGTTAA | AGCAGTGGCA | 660
| CAAGTAGCAG | AATTAAGAGG | AGATAAGTGG | TATGTTGATC | TAGATAATGT | ACAAATAGTT | 720
| AAAAAACATG | GTGGTAGCAT | TAATGATACT | CAATTAGTAT | ACGGCATAGT | AGTTGATAAG | 780
| GAAGTTGTAC | ATCCGGGCAT | GCCAAGAGG | ATTGAAAATG | CTAAGATAGC | CCTTTTAGAC | 840
| GCTTCATTAG | AAGTTGAGAA | ACCCGAATTG | GATGCAGAAA | TAAGAATTAA | CGATCCAACA | 900
| CAGATGCACA | AATTCTTGGA | AGAAGAAGAA | AACATATTGA | AGAAAAAGT | AGATAAGATT | 960
| GCAGCTACTG | GTGCTAACGT | TGTAATATGC | CAGAAAGGTA | TCGATGAAGT | TGCACAACAC | 1020
| TATTTAGCTA | AGAAAGGTAT | ATTAGCTGTT | AGGAGAGCCA | AGAAGAGTGA | TTTAGAGAAA | 1080
| TTAGCTAGAG | CTACCGGAGG | TAGAGTCATA | TCAAATATTG | ATGAATTAAC | TTCACAAGAT | 1140
| CTAGGTTATG | CCGCATTAGT | GGAAGAGAGA | AAAGTAGGAG | GGATAAGAT | GGTATTCGTA | 1200
| GAAGGTGCAA | AGAATCCAAA | ATCAGTTAGT | ATACTAATAA | GAGGAGGATT | AGAGAGAGTA | 1260
| GTAGATGAGA | CTGAAAGAGC | TCTTAGGGAC | GCTTTAGGTA | CAGTGGCAGA | TGTAATAAGG | 1320
| GATGGTAGAG | CAGTAGCTGG | TGGTGGAGCT | GTTGAGATAG | AGATAGCTAA | GAGATTAAGA | 1380
| AAGTATGCCC | CACAAGTTGG | TGGTAAAGAG | CAATTAGCAA | TTGAAGCATA | TGCTAATGCA | 1440
| ATAGAAGGAC | TTATCATGAT | ATTGGCGGAA | AACGCAGGAT | TAGATCCTAT | AGACAAATTA | 1500
| ATGCAATTAA | GAAGTCTTCA | CGACAATGAG | ACCAATAAAT | GGTATGGACT | TAATTTATTT | 1560
| ACTGGAAATC | CAGAGGATAT | GTGGAAATTA | GGTGTTATTG | AACCGGCACT | AGTGAAAATG | 1620
| AATGCAATTA | AGGCTGCAAC | AGAAGCAGTA | ACATTAGTGT | TAAGAATAGA | TGATATTGTA | 1680
| GCAGCTGGAA | AGAAGGGTGG | AAGTGAGCCA | GGCGGTAAGA | AAGAGAAAGA | AGAAAAGTCC | 1740
| TCTGAAGAC | | | | | | 1749

(2) INFORMATION FOR SEQ ID NO:2:

(i) SEQUENCE CHARACTERISTICS:
      (A) LENGTH: 552 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
      (A) ORGANISM: Sulfolobus shibatae (xi) SEQUENCE DESCRIPTION: SEQ ID NO:2:

```
Met Ala Thr Ala Thr Val Ala Thr Thr Pro Glu Gly Ile Pro Val Ile
 1               5                  10                  15

Ile Leu Lys Glu Gly Ser Ser Arg Thr Tyr Gly Lys Glu Ala Leu Arg
            20                  25                  30
```

| | | | | | | | | | | | | | | |
|---|---|---|---|---|---|---|---|---|---|---|---|---|---|---|
|Ala|Asn|Ile<br>35|Ala|Ala|Val|Lys|Ala<br>40|Ile|Glu|Glu|Ala|Leu<br>45|Lys|Ser|Thr|
|Tyr|Gly<br>50|Pro|Arg|Gly|Met|Asp<br>55|Lys|Met|Phe|Val|Asp<br>60|Ser|Leu|Gly|Asp|
|Ile<br>65|Thr|Ile|Thr|Asn|Asp<br>70|Gly|Ala|Thr|Ile|Leu<br>75|Asp|Lys|Met|Asp|Leu<br>80|
|Gln|His|Pro|Thr|Gly<br>85|Lys|Leu|Leu|Val|Gln<br>90|Ile|Ala|Lys|Gly|Gln<br>95|Asp|
|Glu|Glu|Thr|Ala<br>100|Asp|Gly|Thr|Lys|Thr<br>105|Ala|Val|Ile|Leu|Ala<br>110|Gly|Glu|
|Leu|Ala|Lys<br>115|Lys|Ala|Glu|Asp|Leu<br>120|Leu|Tyr|Lys|Glu|Ile<br>125|His|Pro|Thr|
|Ile|Ile<br>130|Val|Ser|Gly|Tyr|Lys<br>135|Lys|Ala|Glu|Glu|Ile<br>140|Ala|Leu|Lys|Thr|
|Ile<br>145|Gln|Asp|Ile|Ala|Gln<br>150|Pro|Val|Ser|Ile|Asn<br>155|Asp|Thr|Asp|Val|Leu<br>160|
|Arg|Lys|Val|Ala|Leu<br>165|Thr|Ser|Leu|Gly|Ser<br>170|Lys|Ala|Val|Ala|Gly<br>175|Ala|
|Arg|Glu|Tyr|Leu<br>180|Ala|Asp|Leu|Val|Val<br>185|Lys|Ala|Val|Ala|Gln<br>190|Val|Ala|
|Glu|Leu|Arg<br>195|Gly|Asp|Lys|Trp|Tyr<br>200|Val|Asp|Leu|Asp|Asn<br>205|Val|Gln|Ile|
|Val|Lys<br>210|Lys|His|Gly|Gly|Ser<br>215|Ile|Asn|Asp|Thr|Gln<br>220|Leu|Val|Tyr|Gly|
|Ile<br>225|Val|Val|Asp|Lys|Glu<br>230|Val|Val|His|Pro|Gly<br>235|Met|Pro|Lys|Arg|Ile<br>240|
|Glu|Asn|Ala|Lys|Ile<br>245|Ala|Leu|Leu|Asp|Ala<br>250|Ser|Leu|Glu|Val|Glu<br>255|Lys|
|Pro|Glu|Leu|Asp<br>260|Ala|Glu|Ile|Arg|Ile<br>265|Asn|Asp|Pro|Thr|Gln<br>270|Met|His|
|Lys|Phe|Leu<br>275|Glu|Glu|Glu|Glu|Asn<br>280|Ile|Leu|Lys|Glu|Lys<br>285|Val|Asp|Lys|
|Ile|Ala<br>290|Ala|Thr|Gly|Ala|Asn<br>295|Val|Val|Ile|Cys|Gln<br>300|Lys|Gly|Ile|Asp|
|Glu<br>305|Val|Ala|Gln|His|Tyr<br>310|Leu|Ala|Lys|Lys|Gly<br>315|Ile|Leu|Ala|Val|Arg<br>320|
|Arg|Ala|Lys|Lys|Ser<br>325|Asp|Leu|Glu|Lys|Leu<br>330|Ala|Arg|Ala|Thr|Gly<br>335|Gly|
|Arg|Val|Ile|Ser<br>340|Asn|Ile|Asp|Glu|Leu<br>345|Thr|Ser|Gln|Asp|Leu<br>350|Gly|Tyr|
|Ala|Ala|Leu<br>355|Val|Glu|Glu|Arg|Lys<br>360|Val|Gly|Glu|Asp|Lys<br>365|Met|Val|Phe|
|Val|Glu<br>370|Gly|Ala|Lys|Asn|Pro<br>375|Lys|Ser|Val|Ser|Ile<br>380|Leu|Ile|Arg|Gly|
|Gly<br>385|Leu|Glu|Arg|Val|Val<br>390|Asp|Glu|Thr|Glu|Arg<br>395|Ala|Leu|Arg|Asp|Ala<br>400|
|Leu|Gly|Thr|Val|Ala<br>405|Asp|Val|Ile|Arg|Asp<br>410|Gly|Arg|Ala|Val|Ala<br>415|Gly|
|Gly|Gly|Ala|Val<br>420|Glu|Ile|Glu|Ile|Ala<br>425|Lys|Arg|Leu|Arg|Lys<br>430|Tyr|Ala|
|Pro|Gln|Val<br>435|Gly|Gly|Lys|Glu|Gln<br>440|Leu|Ala|Ile|Glu|Ala<br>445|Tyr|Ala|Asn|
|Ala|Ile<br>450|Glu|Gly|Leu|Ile|Met<br>455|Ile|Leu|Ala|Glu|Asn<br>460|Ala|Gly|Leu|Asp|
|Pro|Ile|Asp|Lys|Leu|Met|Gln|Leu|Arg|Ser|Leu|His|Glu|Asn|Glu|Thr|

|  | 465 |  |  |  | 470 |  |  |  | 475 |  |  |  | 480 |
|---|---|---|---|---|---|---|---|---|---|---|---|---|---|
| Asn | Lys | Trp | Tyr | Gly 485 | Leu | Asn | Leu | Phe | Thr 490 | Gly | Asn | Pro | Glu | Asp 495 | Met |
| Trp | Lys | Leu | Gly 500 | Val | Ile | Glu | Pro | Ala 505 | Leu | Val | Lys | Met | Asn 510 | Ala | Ile |
| Lys | Ala | Ala 515 | Thr | Glu | Ala | Val | Thr 520 | Leu | Val | Leu | Arg | Ile 525 | Asp | Asp | Ile |
| Val | Ala 530 | Ala | Gly | Lys | Lys | Gly 535 | Gly | Ser | Glu | Pro | Gly 540 | Gly | Lys | Lys | Glu |
| Lys 545 | Glu | Glu | Lys | Ser | Ser 550 | Glu | Asp |